United States Patent [19]

Maurer et al.

[11] Patent Number: 5,092,980
[45] Date of Patent: Mar. 3, 1992

[54] MEASURING APPARATUS FOR DETECTING GASES

[75] Inventors: Christoph Maurer; Hans Matthiessen, both of Bad Schwartau, Fed. Rep. of Germany

[73] Assignee: Drägerwerk Aktiengesellschaft, Lübeck, Fed. Rep. of Germany

[21] Appl. No.: 659,096

[22] Filed: Feb. 22, 1991

[30] Foreign Application Priority Data

Feb. 23, 1990 [DE] Fed. Rep. of Germany ....... 4005761

[51] Int. Cl.$^5$ .............................................. G01N 26/27
[52] U.S. Cl. .................................... 204/415; 204/409; 204/153.17
[58] Field of Search ..................... 204/409, 415, 153.17

[56] References Cited

U.S. PATENT DOCUMENTS

| | | | |
|---|---|---|---|
| 3,787,308 | 1/1974 | Malaspina et al. | 204/415 |
| 4,479,865 | 10/1984 | Beder et al. | 204/415 |
| 4,620,918 | 11/1986 | Bukamier et al. | 204/415 |
| 4,988,429 | 1/1991 | Matthiessen | 204/415 |

FOREIGN PATENT DOCUMENTS 2911548  9/1980  Fed. Rep. of Germany .

*Primary Examiner*—John Niebling
*Assistant Examiner*—Bruce F. Bell
*Attorney, Agent, or Firm*—Walter Ottesen

[57] ABSTRACT

The invention is directed to a measuring apparatus for detecting gases with the aid of an electrochemical sensor with a diffusion barrier being disposed ahead of the sensor. The measuring apparatus is improved in such a manner that the sensor is adaptable with respect to its sensitivity to different measuring ranges during operation without external intervention. The speed of response of the sensor is also increased. Diffusion openings in the diffusion barrier are closable with a valve arrangement associated with the valve openings. The valve arrangement is connected via a valve drive unit to a measurement value comparator for changing the operating position of the particular valve to be actuated.

5 Claims, 2 Drawing Sheets

MEASURING APPARATUS FOR DETECTING GASES

FIELD OF THE INVENTION

The invention relates to a measuring apparatus for detecting gases with the aid of an electrochemical sensor. The electrochemical sensor has an electrolyte chamber with measuring electrodes which is separated from the ambient by a diffusion membrane. A diffusion barrier is interposed ahead of the diffusion membrane and includes at least one diffusion opening changeable with respect to its permeability.

BACKGROUND OF THE INVENTION

A measuring apparatus of this kind with the electrochemical sensor corresponding thereto is disclosed in published German patent application 2,911,548. In this measuring apparatus, the measurement-sensitive surface of the sensor is covered by an exchangeable cap in which several pass-through openings are provided through which the gas to be detected passes to the diffusion membrane thereby making the gas accessible for measurement. In this way, the cap acts as a diffusion barrier which must be exchanged depending upon the concentration of the gas to be detected to thereby prevent the sensor from becoming overloaded with increased concentrations. For this purpose, a plurality of diffusion barriers with different numbers of diffusion openings and/or different cross sections of the diffusion openings are provided. The measuring range must be changed when the quantity of the gas to be detected is either below or above the detection limit of the measuring range then under consideration. If the measuring range must be changed, then the corresponding diffusion barrier must be exchanged. The lower limit of the measuring range corresponds to the detection limit; whereas, the upper limit of the measuring range for the particular diffusion barrier then seated in the apparatus is determined by the quantity of the gas to be detected which is transported in and which can still pass through the diffusion openings. If the quantity of gas transported in exceeds the diffusion capacity of the diffusion barrier, then the measuring apparatus will indicate a measured value which is too low. Furthermore, the characteristic of concentration versus measurement signal is then no longer linear.

In this known apparatus, it is a disadvantage that the adaptation to the different measuring ranges must be carried out manually so that intervention at the sensor takes place each time. Furthermore, the need for an exchange can only then be recognized when the measuring range has already been exceeded. These two requirements interrupt the measurement readiness of the measuring apparatus and make an effective display too slow. The sensor cannot provide a clear signal when the particular measuring range is exceeded in the presence of rapid changes in concentration without the diffusion barrier being first exchanged.

SUMMARY OF THE INVENTION

It is an object of the invention to improve a measuring apparatus of the kind described above so that the sensor is adaptable with respect to its sensitivity to different measuring ranges without an external intervention. It is a further object of the invention to improve such a measuring apparatus so that its speed of response is increased.

According to a feature of the measuring apparatus according to the invention, the diffusion openings are closable with a valve arrangement associated therewith. The valve arrangement is connected via a valve drive unit to a measured value comparator for changing the operating position of the particular valve to be actuated.

The advantage of the invention is seen in that the measurement signal supplied by the sensor to the comparator supplies the necessary information so that the comparator can decide if the measuring range is above or below a limit value region inputted to the comparator. If this limit value region is exceeded, the diffusion opening is correspondingly enlarged in order to provide a larger opening of the diffusion barrier for the increased supply of gas to be detected. The diffusion opening can be changed either in steps in that individual or several valves are opened or closed; or, only a single diffusion opening is provided which however can be held adequately large and which can be continuously increased or reduced and even closed via a displaceable screen. The detecting sensor operates pursuant to a different measuring characteristic in dependence upon the total opening cross section of the diffusion opening.

The circuit of the valve arrangement is controlled by the measured value by means of the comparator. By means of this automatic circuit, it is possible to change over to the corresponding sensor characteristic in dependence upon the required measuring range and to automatically drive the sensor to the characteristic suitable for the measuring range. For the case where several individual valves are switched, a selectable family of characteristics is thereby provided; and, in the case of the single diffusion opening continuously changeable by means of a screen, there is provided a characteristic continuum in which the sensor ca be driven. In this way, a rapid measuring apparatus which reacts automatically to changes in concentration is provided with a wide are of utilization.

The comparator can be provided with a set-value element which is connected in feedback to the valve drive unit. If this is done, the change of the diffusion openings is controlled in such a manner that this set value is always maintained by the sensor. If the concentration value of the gas to be detected drops (which would lead to a drop of the measured value below the set value), the openings are then opened until the sensor supplies a measured value corresponding to the set value. If this does not take place even when the diffusion barrier is opened completely, then this condition can be indicated by an appropriate display unit.

On the other hand, if the concentration of the gas to be detected increases to the point that the adjusted set value is exceeded, then a corresponding number of diffusion openings is closed or the screen is displaced farther over the single diffusion opening until the measurement signal of the sensor coincides with the set value. An arrangement of this kind makes it possible to compensate for even slight deviations from the set value by a corresponding counter control which affects the size of the diffusion openings in the diffusion barrier so that for one embodiment, the number of opened or closed valves becomes a measure for the concentration of the gas to be detected while for the other embodiment, the path moved through by the screen for opening or closing the single opening acts as a measure for the concentration of the gas to be detected. A sensor connected in this manner responds to changing concentration values very rapidly even though the sensor can be slow when viewed in the context of its electrochemical characteristics until it would reach the corresponding saturation measured value. It is no longer necessary to wait until the sensor reaches its saturated measured value to obtain a measured value; instead, the entire measuring apparatus controls directly back to the adjusted measurement signal set value.

An especially advantageous application for a circuit arrangement of this kind is provided in that, to protect the sensor when it is switched on, first the smallest diffusion opening is cleared to determine whether the gas to be detected is even present. If the gas is indeed present, then the diffusion barrier is opened more or less in correspondence to the measurement signal. If no gas is present or the measurement signal is below an indicating threshold, then the maximum opening cross section of the diffusion barrier can be cleared to rapidly reduce the opening cross section when the gas to be measured does appear so that the pregiven set value of the measurement signal is reached.

It is advantageous to configure the openings of the diffusion barrier as valve seats having different cross sections with these valve seats being closable by respective valve discs separately drivable by the valve drive unit. In this way, a diffusion barrier is obtained which can be mounted directly ahead of the diffusion membrane while taking up the smallest possible dead space. By selectively stepping the cross-sectional openings, for example in binary stepping, it is possible to obtain a very precise and finely stepped family of characteristics which can be reliably selected in a suitable combination of closed or opened valves.

A further advantageous embodiment of the diffusion barrier is provided in that either a single or a plurality of individual diffusion openings are covered by a screen displaceably mounted. A greater or lesser number of diffusion openings is covered by the screen in dependence upon the change of the measurement signal; or, a single diffusion opening is cleared to a greater or lesser extent with respect to its cross section.

A possibility of driving the valve discs especially rapidly is provided in that the discs are configured as closure elements made of piezoceramic to which an electric piezo drive is connected as the valve drive. Diffusion openings configured in this manner afford the advantage that they can be configured to be especially small and even can be configured as microstructured ceramic parts and in that the piezo drive can be actuated virtually free of electric power losses. The dead space of the valves is still further reduced by the small configuration of the piezo parts.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
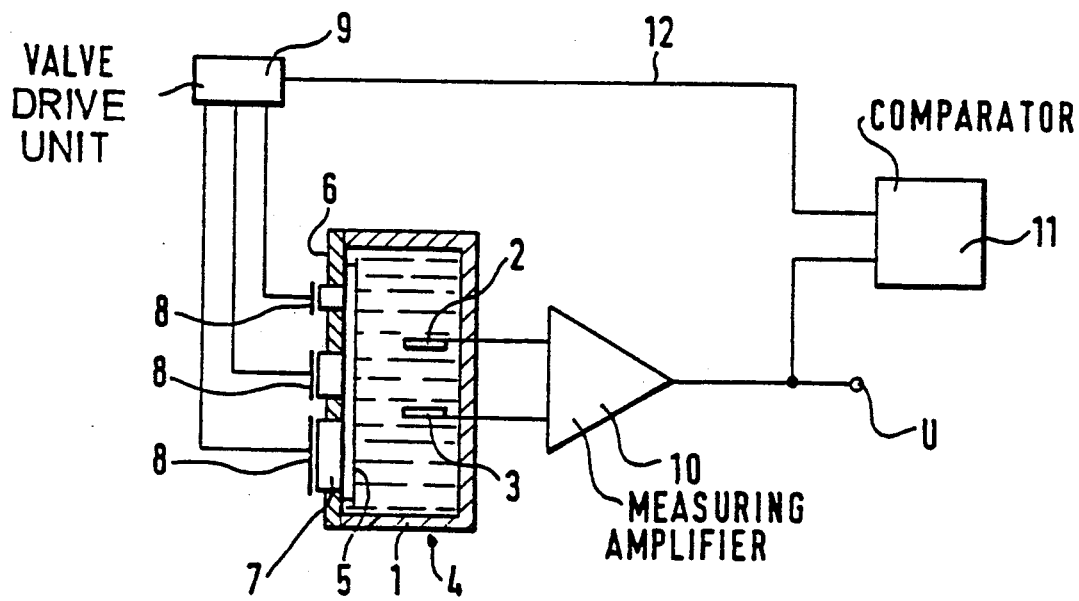
FIG. 1 is a schematic of an embodiment of the measuring apparatus of the invention showing a sensor having a valve arrangement and a measured value comparator.

An electrochemical sensor 1 has a measuring electrode 2 and a counter electrode 3 disposed in electrolyte chamber 4 filled with an electrolyte. The sensor includes a diffusion membrane 5 on the surface facing toward the ambient with the diffusion membrane 5 being covered by a diffusion barrier 6. The diffusion barrier 6 has a plurality of diffusion openings 7 which are each configured as a crater of a valve. The craters are covered by respective valve discs 8 corresponding thereto. The diffusion openings 7 have different opening cross sections and the valve discs 8 are adapted thereto. The valve discs 8 are controlled via respective magnetic valve actuators (not shown) and receive the drive pulses from a valve drive unit 9.

The measurement signal of the sensor 1 is supplied by the measuring electrode 2 and counter electrode 3 to a measuring amplifier 10 and is processed to a measurement output signal U. The output signal U is supplied to a comparator 11 and compared with a limit value set in the comparator 11. If the output signal U exceeds or drops below this limit value, the valve drive unit 9 is driven via the control line 12 and is caused to actuate an appropriate valve disc 8 to open or close the corresponding diffusion opening 7.

Figure 2:
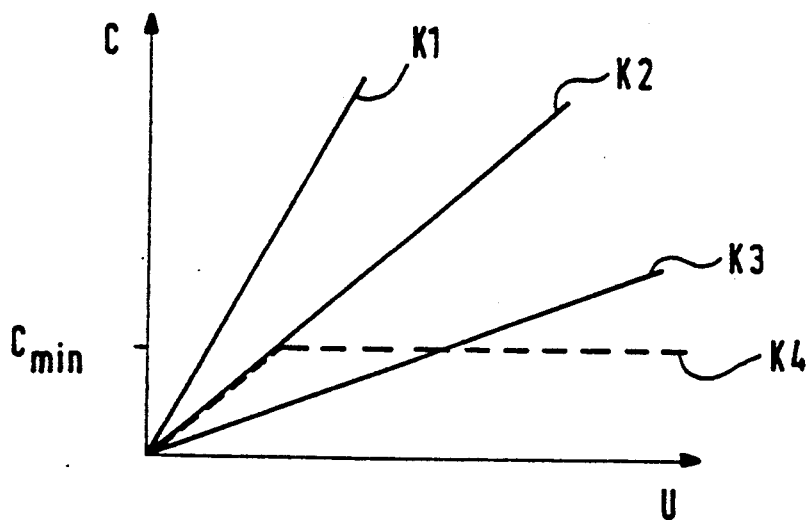
FIG. 2 is a graph of a family of characteristics of the sensor of FIG. 1.

Several different limit values can be stored in the comparator and, when these values are passed through, one or more valve discs 8 are driven separately or in combination with one another so that the sensor can be adapted to the concentration proportions for the gas to be detected which are present in the ambient. The sensor has another characteristic as shown in FIG. 2 depending upon the opening position of the valves (7, 8). Accordingly, the characteristic K1 corresponds to the sensitivity of the sensor 1 when the smallest diffusion opening 7 is opened with the two other openings closed. The characteristic K2 corresponds to the sensitivity of the sensor 1 when the smallest and the intermediate diffusion openings 7 are opened and, the characteristic K3 corresponds to the condition wherein all three diffusion openings 7 are opened. The determination as to which of the valves (7, 8) must be opened or closed in order to maintain the required measurement range is made in accordance with the concentration present by means of the comparison of the measurement signal U with the corresponding limit value at the comparator 11. The operating point of the sensor 1 changes correspondingly from one characteristic to the other. Accordingly, high concentrations are measured along the characteristic K1 while low concentrations are measured along the characteristic K3.

Figure 3:
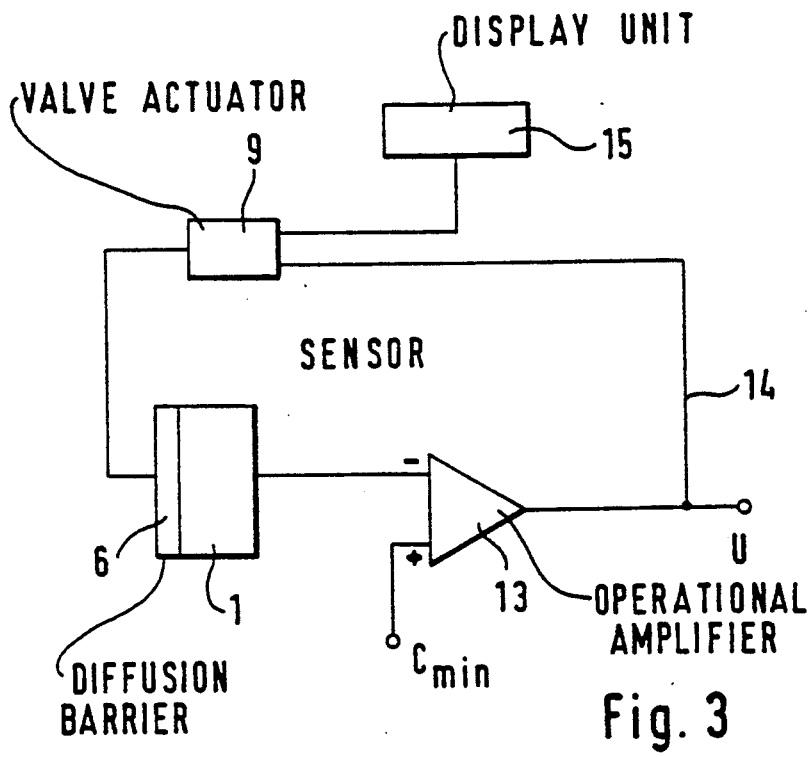
FIG. 3 shows the sensor of FIG. 1 with a compensating circuit.

In FIG. 3, the sensor 1 with its diffusion barrier 6 is connected into a compensating circuit in that its measurement signal is applied to the inverting input of an operational amplifier 13. A constant voltage signal representative of the minimum concentration $C_{MIN}$ which is to be maintained is applied to the non-inverting input of the operational amplifier 13. The output of the operational amplifier 13 is connected via a feedback line 14 to the valve drive unit 9. The operational amplifier 13 supplies a control signal to the valve drive unit 9 when there is a deviation of the signal of sensor 1 at the inverting input of the operational amplifier 13 from a pregiven minimum concentration value. Depending upon the sign of this output signal, this signal reduces the diffusion opening of the diffusion barrier 6 for a positive deviation or increases this opening for a negative deviation of the sensor signal from the minimum concentration value $C_{MIN}$.

A display unit 15 connected to the valve drive unit 9 provides an indication of the degree of opening of the diffusion barrier 6 and this indication can be viewed as being a measure of the gas to be detected which is present. In the circuit arrangement of FIG. 3, the sensor 1 is operated according to characteristic K2 of FIG. 2 for an assumed concentration of the gas to be detected. The minimum concentration value $C_{MIN}$ effective at the operational amplifier 13 provides an upper limit for the characteristic response of the sensor 1 with this response being shown as a thickened line on the characteristic K2 extending from the origin of the coordinate system (C, U) up to the limit $C_{MIN}$. When the sensor 1 reaches the sensor voltage U which corresponds to the minimum concentration value $C_{MIN}$, any further increase of the sensor voltage U does not lead to a further increase of the concentration value along the characteristic K2; instead, the sensor voltage U remains at $C_{MIN}$. The constant trace of the characteristic K4 is obtained in that the valve drive unit 9 influences the diffusion barrier 6 so that the diffusion openings only permit so much gas to pass as is required for maintaining the minimum concentration value $C_{MIN}$.

Figure 4:
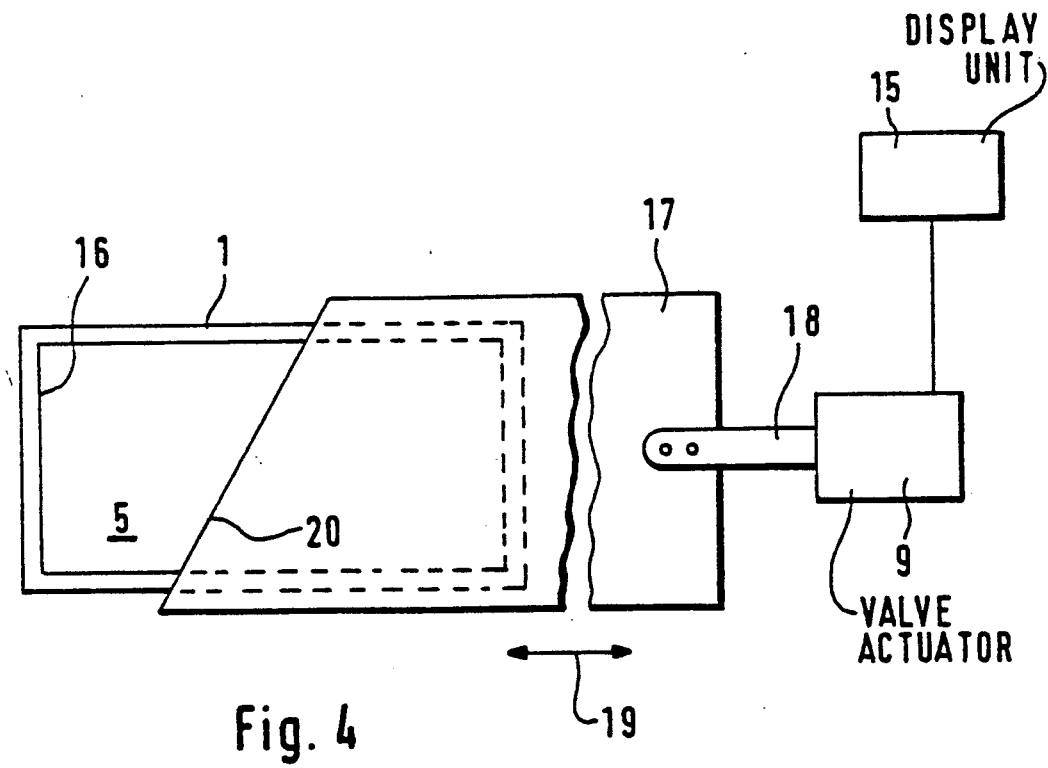
FIG. 4 is a plan view of the sensor provided with a displaceable screen over its diffusion opening.

In the embodiment of FIG. 4, the diffusion barrier has only one single diffusion opening 16 exposing the membrane 5 in the housing of the sensor 1. The diffusion opening 16 corresponds in this case with the housing opening of the sensor 1. A screen 17 is provided as the movable diffusion valve member and is connected to the valve drive unit 9 via a linear guide 18. The position of the linear guide 18 is indicated by the display unit 15 so that the display unit provides a direct measure for the concentration of the gas to be detected.

The sensor 1 of FIG. 4 can be wired in accordance with the schematic of FIG. 1 or in correspondence to the schematic of FIG. 3 and is therefore not repeated in FIG. 4. The screen 17 is displaced more or less by means of the valve drive unit 9 in both directions of the directional arrow 19 in dependence upon whether a comparison value in the comparator 16 or a minimum concentration value $C_{MIN}$ at the operational amplifier 13 is exceeded or if there is a drop therebelow. The diffusion opening 16 is exposed in correspondence to the displacement of the screen 17. The screen 17 lies in seal tight engagement with the edge of the housing of the sensor 1. The edge 20 of the screen 17 is slanted and slides over the membrane 5 in order to obtain as high a sensitivity as possible with reference to the linear movement of the linear guide 18 and the exposed diffusion opening 16 in the range of small opening cross sections.

It is understood that the foregoing description is that of the preferred embodiments of the invention and that various changes and modifications may be made thereto without departing from the spirit and scope of the invention as defined in the appended claims.

What is claimed is:

1. A measuring apparatus for detecting a gas present in the ambient, the measuring apparatus comprising:
   an electrochemical sensor unit including:
   an electrolyte chamber for accommodating an electrolyte therein;
   measuring electrode means disposed in said electrolyte chamber for providing a measurement signal;
   a diffusion membrane separating said electrolyte chamber from the ambient;
   a diffusion barrier assembly interposed between said diffusion membrane and the ambient;
   said diffusion barrier assembly including pass-through opening means having a cross section for allowing the gas to pass therethrough to said diffusion membrane;
   valve means for adjusting said cross section in size so as to permit more or less amounts of the gas to pass to said diffusion membrane; and,
   comparator means for comparing said measurement signal with a limit value and for driving said valve means whereby said cross section of said opening is changed in dependence upon the comparison to said limit value.

2. The measuring apparatus of claim 1, wherein:
   said valve means including movable valve body means for coacting with said opening means; and, a valve drive unit for driving said valve body means to adjust said cross section of said opening means;
   said comparator means includes: a set-value element for supplying a set value to said comparator; and,
   said apparatus further comprising a feedback circuit including said set-value element; and, said feedback circuit being connected between said measuring electrode means and said valve drive unit.

3. The measuring apparatus of claim 1, wherein: said opening means includes: a wall interposed between said diffusion membrane and the ambient; and, a plurality of valve openings having respective different cross sections formed in said wall; and,
   said valve means includes: a plurality of valve discs for opening and closing corresponding ones of said valve openings and, a valve drive unit to selectively drive said valve discs to adjust the overall cross section through which the gas passes to said diffusion membrane.

4. The measuring apparatus of claim 3, said valve discs being configured as respective closure elements made of piezoceramic; and, said valve drive unit being an electric piezo drive connected to corresponding ones of said closure elements.

5. The measuring apparatus of claim 2, wherein:
   said opening means includes a frame interposed between said diffusion membrane and the ambient; and, said frame defining an opening having a predetermined cross section; and,
   said valve means includes: a screen mounted so as to be movable across said opening; and, a valve drive unit operatively connected to said screen for moving said screen over said opening to vary the cross section thereof through which the gas passe to said diffusion membrane.

* * * * *

UNITED STATES PATENT AND TRADEMARK OFFICE
CERTIFICATE OF CORRECTION

PATENT NO. : 5,092,980

DATED : March 3, 1992

INVENTOR(S) : Christoph Maurer and Hans Matthiessen

It is certified that error appears in the above-identified patent and that said Letters Patent is hereby corrected as shown below:

In column 2, line 37: delete "ca" and substitute -- can -- therefor.

In column 2, line 40: delete "are" and substitute -- area -- therefor.

In column 6, line 60: delete "passe" and substitute -- passes -- therefor.

Signed and Sealed this

Fourth Day of May, 1993

Attest:

MICHAEL K. KIRK

*Attesting Officer*   Acting Commissioner of Patents and Trademarks